United States Patent [19]

Mueller et al.

[11] Patent Number: 4,931,540

[45] Date of Patent: Jun. 5, 1990

[54] POLYMERS PREPARED FROM 4,4'-BIS[2-(3,4-(DICARBOXYPHENYL)HEXA-FLUOROISOPROPYL] DIPHENYL ETHER DIANHYDRIDE

[75] Inventors: Werner H. Mueller, E. Greenwich; Dinesh N. Khanna; Rohitkumar H. Vora, both of W. Warwick, all of R.I.; Ruediger J. Erckel, Warren, N.J.

[73] Assignee: Hoechst Celanese Corporation, Somerville, N.J.

[21] Appl. No.: 124,720

[22] Filed: Nov. 24, 1987

[51] Int. Cl.$^5$ ........................ C08G 69/26; C08G 8/02; C08G 14/00

[52] U.S. Cl. ..................................... 528/353; 528/125; 528/126; 528/128; 528/172; 528/173; 528/229; 528/352

[58] Field of Search ............... 528/353, 172, 352, 125, 528/126, 128, 229, 173

[56] References Cited

U.S. PATENT DOCUMENTS

| | | | |
|---|---|---|---|
| 3,890,272 | 1/1975 | D'Alelio | 528/353 |
| 4,395,514 | 7/1983 | Edelman | 528/353 |
| 4,552,931 | 11/1985 | St. Clair et al. | 528/353 |
| 4,668,766 | 5/1987 | Treybig | 528/353 |

*Primary Examiner*—John Kight, III
*Assistant Examiner*—M. L. Moore
*Attorney, Agent, or Firm*—Perman & Green

[57] ABSTRACT

This invention relates to new fluorine-containing polyimides, polyamide-acids/esters, polyamides, addition polyimides and imide oligomers which exhibit low melting points, better solubilities, low dielectric constants, superior thermal and thermal oxidative stability, and improved processing characteristics.

The products of this invention are characterized by the fact that they are derived from 4,4'-bis[2-(3,4-(dicarboxyphenyl)hexafluoroisopropyl]diphenyl ether dianhydride.

40 Claims, No Drawings

4,931,540

POLYMERS PREPARED FROM 4,4'-BIS[2-(3,4-DICARBOXYPHENYL)HEXA-FLUOROISOPROPYL] DIPHENYL ETHER DIANHYDRIDE

FIELD OF THE INVENTION

This invention relates to new fluorine-containing polyimides, polyamide-acids/esters, addition polyimides and imide oligomers which exhibit low melting points, better solubilities, low dielectric constants, superior thermal and thermal oxidative stability, and improved processing characteristics.

BACKGROUND OF THE INVENTION

Polyimides are widely used in the aerospace industry and electronics industry, because of their toughness, low density, thermal stability, radiation resistance and mechanical strength. However, it is recognized that polyimides are difficult to process. The processing problems arise from the insolubility of polyimides in most of the more common solvents. Consequently, products were fabricated from polyamide-acid intermediates, which are more soluble but less stable, and then imidized to provide the desired end product. The disadvantage of this process is that the water liberated during the imidization of the polyamide-acid forms undesirable voids or surface irregularities in the final product which reduce its mechanical properties.

Another approach is to provide a fully imidized prepolymer having reactive end groups. In this way, the water formed during imidization is removed before the final cure of the prepolymer. The resulting polyimide product is typically a thermoset plastic. However, the imidized prepolymers are not as soluble as would be desired.

It has been suggested that polyimides having a single hexafluoroisopropylidene linking group in the diamine or dianhydride comonomers have improved solubility properties. Several patents disclose polyimides prepared from diamines of this type. For example, U.S. Pat. No. 3,356,648 to Rogers discloses polyimides prepared from 2,2-bis(4-aminophenyl) hexafluoropropane and 2,2-bis(3,4-dicarboxyphenyl) hexafluoropropane dianhydride; U.S. Pat. No. 3,959,350 to Rogers discloses polyimides prepared from 2,2-bis(3,4-dicarboxyphenyl) hexafluoropropane and other diamines; U.S. Pat. No. 4,592,925 to DuPont et al. discloses polyimides prepare from 2,2-bis(3-aminophenyl) hexafluoropropane; U.S. Pat. No. 4,111,906 to Jones et al. discloses polyimides prepared from 2,2-bis[4-(4-aminophenoxy)phenyl] hexafluoropropane; and U.S. Pat. No. 4,477,648 to Jones et al. discloses polyimides prepared from 2,2-bis[(2-halo-4-aminophenoxy)phenyl] hexafluoropropane and a dianhydride including, inter alia, 2,2-bis(3,4-dicarhoxyphenyl)-hexafluoropropane dianhydride.

SUMMARY OF THE INVENTION

The present invention seeks to provide polyimides and oligomers having improved solubility and processing characteristics by incorporating into the polymeric chain a novel aromatic dianhydride compound having two hexafluoroisopropylidene linking groups. The dianhydride may be characterized as having the formula:

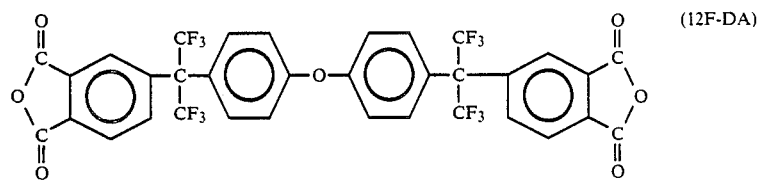
(12F-DA)

The polyimides are prepared by reacting this dianhydride or the corresponding tetracarboxylic acid or diacid-diester with diamines. It has been found that the polyimides of this invention have low dielectric constants and superior thermal and thermo-oxidative stability.

In another aspect, the invention also provides new monomers, oligomers and their corresponding addition polyimides. The monomers and oligomers are formed by reacting the new dianhydride with diamines and reactive end-capping compounds such as aromatic ethynyl amines, nadic anhydrides, benzocyclobutene amines, or maleic anhydrides. The resulting imide monomers and oligomers may then be cured by addition reactions.

In yet another aspect, the invention provides polymer precursor compositions, epoxy resin hardeners, matrix resins, composites, laminates, films, fibers, adhesives, coatings, photoresists and molded articles.

DETAILED DESCRIPTION OF THE INVENTION

The polyimides of this invention may be characterized as having recurring groups of the structure:

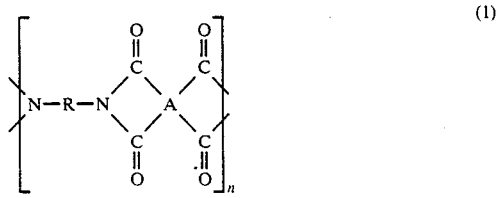
(1)

wherein n is the number of repeating groups, R is a divalent organic radical, and A is

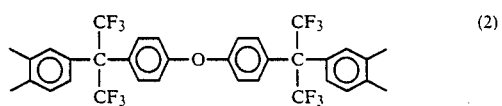
(2)

These polyimides may be prepared by reacting diamines with tetracarboxylic acids or derivatives of the formula:

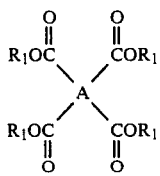

(3)

or a dianhydride of the formula:

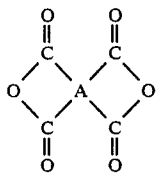

(4)

wherein A is a radical of formula (2), and $R_1$ is hydrogen or a monovalent organic radical, preferably hydrogen. When $R_1$ is a monovalent organic radical, $R_1$ is preferably a lower ($C_1$-$C_8$) alkyl or substituted alkyl group.

EXAMPLE 1

Preparation of 4,4'-bis[2-(3,4-Dicarboxyphenyl) Hexafluoroisopropyl] Diphenyl Ether Dianhydride To a stainless steel reactor 4,4'-bis(2-hydroxyhexafluoroisopropyl) diphenyl ether, o-xylene and hydrogen fluoride are charged in a molar ratio of at least 1:2:10. The reaction mixture is stirred in the closed reactor under autogenous pressure at temperatures of between 100 and 170° C. for 24 to 96 hours. After evaporation of the hydrogen fluoride at 80° C. the contents of the reactor are poured into ice. The organic layer is then separated, diluted with methylene chloride, and dried over calcium chloride. After evaporation of the solvent, the crude product is treated with charcoal in chloroform, filtered and recrystallized. The 4,4'-bis[2-(3,4-dimethylphenyl)hexafluoroisopropyl]-diphenyl ether has a melting point 139–141° C. The thusly obtained diphenyl ether is dissolved in acetic acid and charged to a glass pressure vessel. A catalytic amount of a solution of Co(OAc)$_2$.4H$_2$O, Mn(OAc)$_2$.4H$_2$O, HBr and acetic acid is added. The reaction mixture is heated up to 180° C. under oxygen at a pressure of 7.5 bar. The exothermic reaction starts at about 90° C. with oxygen uptake and is finished in 2 hours at 180° C. The reaction product is then treated with a small amount of oxalic acid dihydrate in acetic acid. After heating the mixture to reflux temperature for 2 hours, the solution is filtered. Acetic acid and water are distilled off. Acetic acid anhydride is added to the residue and the solution is heated to 120° C. for one hour. After cooling to room temperature, the crystalline product is isolated, washed three times with a mixture of acetic acid and its anhydride, and dried in vacuo yielding 4,4'-bis[2-(3,4-dicarboxyphenyl)hexafluoroisopropyl]-diphenyl ether dianhydride. M.P.168°–170° C.

The tetracarboxylic acids or derivatives of formulae (3) or (4) may be reacted with diamines having a formula:

$$H_2N-R-NH_2 \quad (5)$$

wherein R is a divalent organic radical. Preferably R comprises an aromatic moiety such as a phenylene or naphthalene group which may comprise substituent halogen, hydroxy or lower alkyl ($C_1$-$C_6$) groups. Preferably R is selected from the group consisting of

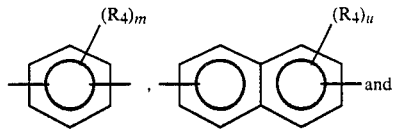

and

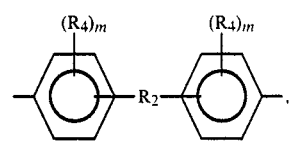

wherein $R_2$ is a carbon-carbon bond, —O—, —S—,

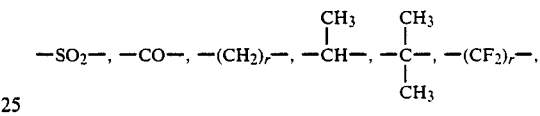

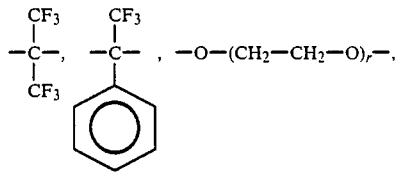

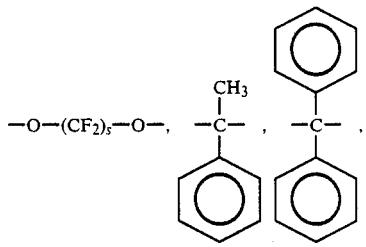

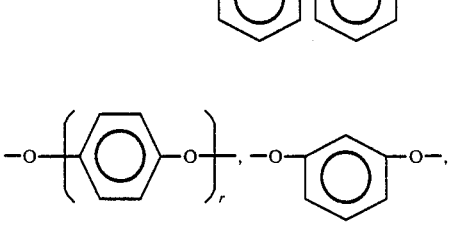

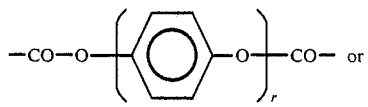

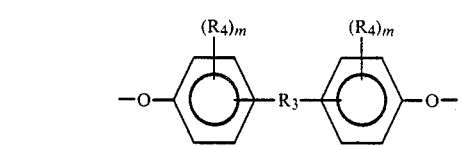

wherein $R_3$ is a carbon-carbon bond, —S—, —SO$_2$—, —CO—, —CH$_2$—, —C$_2$H$_4$—,

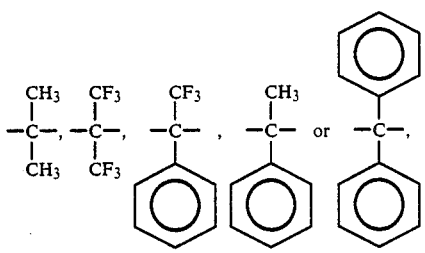

$R_4$ is halogen, hydroxy, lower ($C_1$-$C_6$) alkyl, or lower ($C_1$-$C_6$) alkoxy, m is 0 to 4, preferably m is 0, r is 1 to 4, s is 1 to 5, and u is 0 to 6, preferably u is 0.

Illustrative of diamines which are suitable for use in the present invention are:
m-phenylene diamine;
p-phenylene diamine;
1,3-bis(4-aminophenyl) propane;
2,2-bis(4-aminophenyl) propane;
4,4'-diamino-diphenyl methane;
1,2-bis(4-aminophenyl) ethane;
1,1-bis(4-aminophenyl) ethane;
2,2'-diamino-diethyl sulfide;
bis(4-aminophenyl) sulfide;
2,4'-diamino-diphenyl sulfide;
bis(3-aminophenyl) sulfone;
bis(4-aminophenyl) sulfone;
4,4'-diamino-dibenzyl sulfoxide;
bis(4-aminophenyl) ether;
bis(3-aminophenyl) ether;
bis(4-aminophenyl) diethyl silane;
bis(4-aminophenyl) diphenyl silane;
bis(4-aminophenyl) ethyl phosphine oxide;
bis(4-aminophenyl) phenyl phosphine oxide;
bis(4-aminophenyl)-N-phenylamine;
bis(4-aminophenyl)-N-methylamine;
1,2-diamino-naphthalene;
1,4-diamino-naphthalene;
1,5-diamino-naphthalene;
1,6-diamino-naphthalene;
1,7-diamino-naphthalene;
1,8-diamino-naphthalene;
2,3-diamino-naphthalene;
2,6-diamino-naphthalene;
1,4-diamino-2-methyl-naphthalene;
1,5-diamino-2-methyl-naphthalene;
1,3-diamino-2-phenyl-naphthalene;
4,4'-diamino-biphenyl;
3,3'-diamino-biphenyl;
3,3'-dichloro-4,4'-diamino-biphenyl;
3,3'-dimethyl-4,4'-diamino-biphenyl;
3,4'-dimethyl-4,4'-diamino-biphenyl;
3,3'-dimethoxy-4,4'-diamino-biphenyl;
4,4'-bis(4-aminophenoxy)-biphenyl;
2,4-diamino-toluene;
2,5-diamino-toluene;
2,6-diamino-toluene;
3,5-diamino-toluene;
1,3-diamino-2,5-dichloro-benzene;
1,4-diamino-2,5-dichloro-benzene;
1-methoxy-2,4-diamino-benzene;
1,4-diamino-2-methoxy-5-methyl-benzene;
1,4-diamino-2,3,5,6-tetramethyl-benzene;
1,4-bis(2-methyl-4-amino-pentyl)-benzene;
1,4-bis(1,1-dimethyl-5-amino-pentyl)-benzene;
1,4-bis(4-aminophenoxy)-benzene;
o-xylylene diamine;
m-xylylene diamine;
p-xylylene diamine;
3,3'-diamino-benzophenone;
4,4'-diamino-benzophenone;
2,6-diamino-pyridine;
3,5-diamino-pyridine;
1,3-diamino-adamantane;
3,3'-diamino-1,1'-diadamantane;
bis(4-amino-cyclohexyl) methane;
1,5-diamino-pentane;
1,6-diamino-hexane;
1,7-diamino-heptane;
1,8-diamino-octane;
1,9-diamino-nonane;
1,10-diamino-decane;
1,7-diamino-3-methyl-heptane;
1,7-diamino-4,4-dimethyl-heptane;
2,11-diamino-dodecane;
1,3-bis(3-aminopropoxy) ethane;
1,3-diamino-2,2-dimethyl-propane;
1,6-diamino-3-methoxy-hexane;
1,6-diamino-2,5-dimethyl-hexane;
1,7-diamino-2,5-dimethyl-heptane;
1,9-diamino-5-methyl-nonane;
1,4-diamino-cyclohexane;
2,5-diamino-1,3,4-oxadiazole;
N-(3-aminophenyl)-4-aminobenzamide;
4-aminophenyl-3-aminobenzoate;
2,2-bis(4-aminophenyl) hexafluoropropane;
2,2-bis(3-aminophenyl) hexafluoropropane;
2,2-bis[4-(4-aminophenoxy)phenyl]hexafluoropropane;
2,2-bis[4-(2-chloro-4-aminophenoxy)phenyl] hexafluoropropane;
1,1-bis(4-aminophenyl)-1-phenyl-2,2,2-trifluoroethane;
1,1-bis[4-(4-aminophenoxy)phenyl]-1-phenyl-2,2,2-trifluoroethane;1,
4-bis(3-aminophenyl)buta-1-ene-3-yne;
1,3-bis(3-aminophenyl)hexafluoropropane;
1,5-bis(3-aminophenyl)decafluoropentane; and
mixtures thereof.

A mixture of at least two suitable diamines may be reacted with a tetracarboxylic acid or derivative of formulae (3) or (4) to produce copolyimides.

Preferred polyimides are those prepared from the tetracarboxylic acids or derivatives of formulae (3) or (4) and diamines such as 2,2-bis(4-aminophenyl) hexafluoropropane, 2,2-bis(3-aminophenyl) hexafluoropropane, 2,2-bis[4-(4-aminophenoxy)-phenyl]hexafluoropropane, bis(4-aminophenyl) ether, m-phenylene diamine and p-phenylene diamine.

A preferred process for preparing the polyimides of this invention involves first preparing a polyamide-acid by reacting the diamine and the tetracarboxylic acid or derivative such as the dianhydride in an organic solvent, preferably under substantially anhydrous conditions for a time and at a temperature sufficient to provide at least 50% of the corresponding polyamide-acid, and then converting the polyamide-acid to the polyimide. Suitable conditions for reacting the diamine and the dianhydride are disclosed in detail in U.S. Pat. Nos. 3,356,648 and 3,959,350, both to Rogers, which are incorporated herein by reference. The intermediate polyamide-acid may also be esterified to provide polyamide-esters.

The polyamide-acids/esters may be characterized as having recurring groups of the structure:

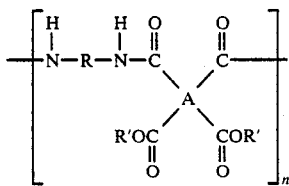

(6)

wherein n is the number of repeating groups, A is a tetravalent radical of formula (2), R is a divalent organic radical as defined above and R' is hydrogen or a monovalent organic radical. In addition to being useful to produce polyimides, the polyamide-acids may be esterified with thermally polymerizable or photopolymerizable compounds such as olefinically unsaturated monoepoxides to produce polyamide-esters useful in photoresist compositions.

The polyamide-acids/esters may be cyclicized to form polyimides. Conversion to the polyimides may be accomplished by a heat treatment, a chemical treatment or both as described in the above-referenced Rogers patents.

In a preferred process for preparing the polyimides, the diamine and dianhydride are reacted in gamma-butyrolactone (BLO), or a mixture of BLO and another solvent such as diglyme. The resulting product is a polyamide-acid which is then converted to the desired polyimide by one of several methods: heating the polyamide-acid solution until imidization is substantially complete; or by combining the polyamide-acid solution and a dehydrating agent, with or without catalyst, and optionally heating the resulting mixture until imidization is substantially complete. The use of the BLO solvent provides several advantages in that it avoids the formation of complexes of the polyamide-acid and the solvent that typically occur when solvents such as N-methyl pyrrolidone (NMP) are used and allows the removal of the solvent to proceed at lower temperatures (below 250° C.) to obtain uniform films. When mixed with diglyme, the ratio by volume of BLO to diglyme is preferably in the range of about 10:90 to 90:10, more preferably of about 40:60 to 60:40.

The following examples are illustrative of the invention:

EXAMPLE 2

To a 250 ml reaction unit fitted with a condenser, thermometer, stirrer and nitrogen blanket, and purged with nitrogen, 6.68 g (0.02 moles) of 2,2-bis(4-aminophenyl) hexafluoropropane (hereinafter "6F-44") are charged along with 25 g of distilled N-methyl pyrrolidone (NMP) under nitrogen atmosphere. The mixture is stirred to get a clear solution. To the clear, very pale yellow color solution, 15.24 g (0.02 moles) of 4,4'-bis[2-(3,4-dicarboxyphenyl) hexafluoroisopropyl] diphenyl ether dianhydride (hereinafter "12F-DA") are charged while stirring is continued. 63 g of NMP are added to the reaction mixture which is then stirred overnight at room temperature. The resulting polyamic acid has inherent viscosity of 0.60 dl/g, measured at 0.5 g/dl at 25° C. in dimethyl acetamide (DMAc). 26.4 g of acetic anhydride and 2.65 g of 3-picoline are added to 102.61g of the polyamic acid solution. The reaction is stirred at room temperature for about six hours and the resulting polyimide is precipitated in methanol, isolated by filtration, washed with fresh methanol, and dried overnight in a vacuum oven at 85° C. It is soluble in acetone, DMAc, diglyme, MEK, NMP, THF, chloroform, BLO solvents.

A film is prepared from a solution comprising 20% by weight solids in a 50/50 mixture by volume of BLO/diglyme and cured to 350° C. by stepwise heating. A very pale yellow, clear, flexible, self-supporting, tough film is obtained. Its glass transition temperature ($T_g$) is 263° C. by differential scanning calorimetry (DSC) and 5% weight loss is at 527° C. by thermal gravimetric analysis (TGA). Tensile strength is about 11300 psi at room temperature. Tensile modulus is about 270 Ksi at room temperature, elongation at break is about 8% at room temperature, and it has a limiting oxygen index of 48.

EXAMPLES 3-8

Polyimides are prepared in accordance with the procedure set forth in Example 2 by reacting the 12F-DA dianhydride with the following diamines:
2,2-bis(3-aminophenyl) hexafluoropropane (6F-33),
2,2-bis[4-(4-aminophenoxy)phenyl]hexafluoropropane (BDAF),
bis(4-aminophenyl) ether (ODA),
o-tolidine (DDMB),
m-phenylene diamine (mPDA), and
p-phenylene diamine (pPDA).

The properties of the resulting polyimides are shown in Table 1.

TABLE 1

| Example Number<br>Dianhydride | | 3<br>6F-33 | 4<br>BDAF | 5<br>ODA | 6<br>DDMB | 7<br>mPDA | 8<br>pPDA |
|---|---|---|---|---|---|---|---|
| | Units | | | | | | |
| Ratio of 12F-DA/Diamine | millimole/millimole | 20/20 | 20/20 | 25/25 | 30/30 | 30/30 | 12.5/12.5 |
| Inherent Viscosity (Polyamic Acid) | dl/g at 25° C. in DMAc | 0.41 | 0.64 | 0.57 | 0.66 | 0.65 | 0.51 |
| Inherent Viscosity (Polyimide) | dl/g at 25° C. in DMAc | 0.35 | 0.57 | 0.49 | 0.52 | 0.40 | 0.44 |
| Glass Transition Temp. (Tg) | °C. | 226 | 233 | 254 | N/D | 260 | 268 |
| 5% Weight loss in air (TGA) | °C. | 520 | 525 | 520 | 500 | 524 | 531 |
| Tensile Strength at room temp. | psi | 7,400 | 9,200 | 13,700 | 17,100 | 15,500 | 13,200 |
| Tensile Modulus at room temp. | Ksi | 360 | 280 | 280 | 410 | 340 | 270 |

TABLE 1-continued

| Example Number | | 3 | 4 | 5 | 6 | 7 | 8 |
|---|---|---|---|---|---|---|---|
| Dianhydride | | 6F-33 | BDAF | ODA | DDMB | mPDA | pPDA |
| Elongation at break | % | 2.7 | 10.9 | 8.9 | 6.2 | 8.3 | 12.0 |

The polyimides exhibit good solubility properties in solvents such as N-methyl pyrrolidone (NMP), dimethyl acetamide (DMAc), diglyme, methylethylketone (MEK), tetrahydrofuran (THF), acetone, chloroform, butyrolactone (BLO), dimethylsulfoxide (DMS), dimethylformamide (DMF) and the like.

The polyimides of this invention may be molded using standard techniques such as compression molding or injection molding to produce melt fabricated articles such as safety masks, windshields, electronic circuit substrates, airplane windows or the like. They may be compounded with graphite, graphite fiber, molybdenum disulphide or PTFE for the production of self-lubricating wear surfaces useful for piston rings, valve seats, bearings and seals. They may also be compounded with fibers such as glass, graphite or boron fibers to produce molding compounds for high strength structural components such as jet engine components. The polyimides may also be compounded with friction materials to produce molding compounds for high temperature braking components or with abrasive materials such as diamonds for high speed grinding wheels.

The polyimides may be cast as films useful as wire and cable wraps, motor slot liners or flexible printed circuit substrates. They may be used as coatings on substrates such as aluminum or silicone dioxide. They are also useful to produce high temperature coatings for magnetic wire, dip coatings for various electronic components, protective coatings over glass, metal and plastic substrates, wear coatings, and photoresist coatings useful in microelectronic processing.

The polyimides may also be used to produce high temperature adhesives for bonding aerospace structures or electrical circuitry, conductive adhesives when mixed with conductive fillers such as silver or gold for microelectronic applications, or adhesives for glass, metal or plastic substrates.

They may be used as varnish compositions or matrix resins to produce composites and laminates. The varnish compositions and matrix resins may be used to impregnate glass or quartz cloth, or graphite or boron fibers, for the production of radomes, printed circuit boards, radioactive waste containers, turbine blades, aerospace structural components or other structural components requiring high temperature performance, non-flammability and excellent electrical properties.

The invention also provides new copolyamideacids/-esters and copolyimides. The copolymers are prepared by reacting diamine of formula (5) with a mixture of at least one tetracarboxylic acid or derivative of formulae (3) or (4) and at least one tetracarboxylic acid or ester having the formula:

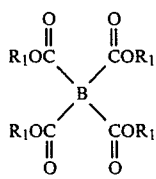

(7)

or dianhydride having the formula:

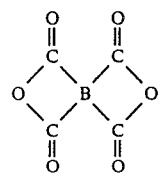

(8)

wherein B is a tetravalent organic radical having at least 4 carbon atoms and $R_1$ is as defined above. Preferably B comprises an aromatic moiety such as a phenylene or naphthalene group which may comprise substituent halogen, hydroxy or lower ($C_1$-$C_6$) alkyl or lower ($C_1$-$C_6$) alkoxy groups.

Preferably B is selected from the group consisting of:

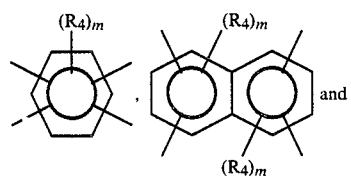

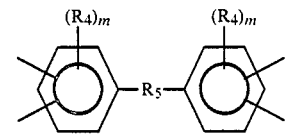

wherein $R_5$ is a carbon-carbon bond, —O—, —S—,

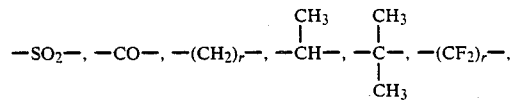

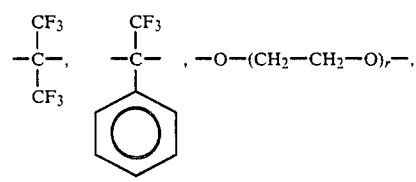

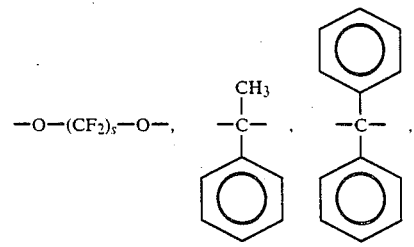

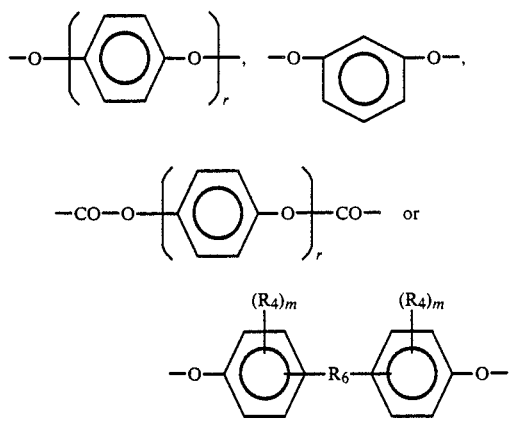

wherein $R_6$ is a carbon-carbon

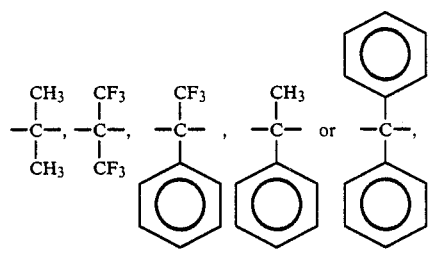

$R_4$ is halogen, hydroxy, lower ($C_1$–$C_6$) alkyl or lower ($C_1$–$C_6$) alkoxy, m is 0 to 3, preferably m is 0, r is 1 to 4, and s is 1 to 5.

Illustrative of tetracarboxylic acid dianhydrides which are suitable for use in the present invention are:
1,2,4,5-benzene tetracarboxylic acid dianhydride;
1,2,3,4-benzene tetracarboxylic acid dianhydride;
1,4-bis(2,3-dicarboxyphenoxy) benzene dianhydride;
1,3-bis(3,4-dicarboxyphenoxy) benzene dianhydride;
1,2,4,5-naphthalene tetracarboxylic acid dianhydride;
1,2,5,6-naphthalene tetracarboxylic acid dianhydride;
1,4,5,8-naphthalene tetracarboxylic acid dianhydride;
2,3,6,7-naphthalene tetracarboxylic acid dianhydride;
2,6-dichloronaphthalene-1,4,5,8-tetracarboxylic acid dianhydride;
2,7-dichloronaphthalene-1,4,5,8-tetracarboxylic acid dianhydride;
2,3,6,7-tetrachloronaphthalene-1,4,5,8-tetracarboxylic acid dianhydride;
3,3',4,4'-diphenyl tetracarboxylic acid dianhydride;
2,2',3,3'-diphenyl tetracarboxylic acid dianhydride;
4,4'-bis(3,4-dicarboxyphenoxy)diphenyl dianhydride;
bis(2,3-dicarboxyphenyl) ether dianhydride;
4,4'-bis(2,3-dicarboxyphenoxy) diphenyl ether dianhydride;
4,4'-bis(3,4-dicarboxyphenoxy) diphenyl ether dianhydride;
bis(3,4-dicarboxyphenyl) sulfide dianhydride;
4,4'-bis(2,3-dicarboxyphenoxy) diphenyl sulfide dianhydride;
4,4'-bis(3,4-dicarboxyphenoxy) diphenyl sulfide dianhydride;
bis(3,4-dicarboxyphenyl) sulfone dianhydride;
4,4'-bis(2,3-dicarboxyphenoxy) diphenyl sulfone dianhydride;
4,4'-bis(3,4-dicarboxyphenoxy) diphenyl sulfone dianhydride;
3,3',4,4'-benzophenone tetracarboxylic acid dianhydride;
2,2',3,3'-benzophenone tetracarboxylic acid dianhydride;
2,3,3',4'-benzophenone tetracarboxylic acid dianhydride;
4,4'-bis(3,4-dicarboxyphenoxy) benzophenone dianhydride;
bis(2,3-dicarboxyphenyl)methane dianhydride;
bis(3,4-dicarboxyphenyl)methane dianhydride;
1,1-bis(2,3-dicarboxyphenyl)ethane dianhydride;
1,1-bis(3,4-dicarboxyphenyl)ethane dianhydride;
1,2-bis(3,4-dicarboxyphenyl)ethane dianhydride;
2,2-bis(2,3-dicarboxyphenyl)propane dianhydride;
2,2-bis(3,4-dicarboxyphenyl)propane dianhydride;
2,2-bis[4-(2,3-dicarboxyphenoxy)phenyl]propane dianhydride;
2,2-bis[4-(3,4-dicarboxyphenoxy)phenyl]propane dianhydride;
4-(2,3-dicarboxyphenoxy)-4'-(3,4-dicarboxyphenoxy)-diphenyl-2,2propane dianhydride;
2,2-bis[4-(3,4-dicarboxyphenoxy-3,5-dimethyl)phenyl]-propane dianhydride;
1,2,3,4-butane tetracarboxylic acid dianhydride;
1,2,3,4-cyclopentane tetracarboxylic acid dianhydride;
2,3,4,5-thiophene tetracarboxylic acid dianhydride;
2,3,4,5-pyrrolidine tetracarboxylic acid dianhydride;
2,3,5,6-pyrazine tetracarboxylic acid dianhydride;
1,8,9,10-phenanthrene tetracarboxylic acid dianhydride;
3,4,9,10-perylene tetracarboxylic acid dianhydride;
2,2-bis(3,4-dicarboxyphenyl) hexafluoropropane dianhydride;
1,3-bis(3,4-dicarboxyphenyl)hexafluoropropane dianhydride;
1,1-bis(3,4-dicarboxyphenyl)-1-phenyl-2,2,2-trifluoroethane dianhydride;
2,2-bis[4-(3,4-dicarboxyphenoxy)phenyl]hexafluoropropane dianhydride;
1,1-bis[4-(3,4-dicarboxyphenoxy)phenyl]-1-phenyl-2,2,2-trifluoroethane dianhydride; and mixtures thereof.

Preferably, the molar ratio of tetracarboxylic acid or derivative of formulae (3) or (4) to tetracarboxylic acid or derivative of formulae (7) or (8) is in the range of from about 10:90 to about 99:1, more preferably of from about 50:50 to about 99:1. The diamines of formula (5) are suitable for the preparation of the copolymers of this invention. The copolyimides are useful for the utilities discussed above for the polyimides.

The invention provides new monomers, oligomers, prepolymers and the corresponding addition polyimides prepared therefrom. The monomers, oligomers and prepolymers are prepared by reacting the tetracarboxylic acids or derivatives of formulae (3) or (4), or the precursor condensation product of the tetracarboxylic acids or derivatives of formulae (3) or (4) and the diamines of formula (5), with reactive end-capping compounds such as vinyl aromatic anhydrides, nadic acids or derivatives thereof such as anhydrides or acid-esters, maleic anhydrides, aromatic ethynyl amines, or benzocyclobutene amines.

The monomers, oligomers and prepolymers are useful for adhesive compositions, coating compositions, laminate varnish compositions, and composite matrix resin compositions. They may be reacted by addition polymerization reactions to provide addition polyimides which are useful for coatings, laminates and composites.

One class of addition-type polyimide prepolymers may be characterized as having the following structure:

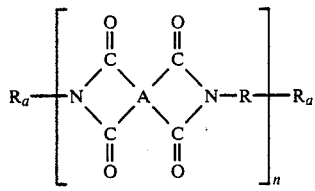
(9)

wherein n is 1 to 5, R is a divalent organic radical as defined above, A is the tetravalent organic radical of formula (2), $R_a$ is

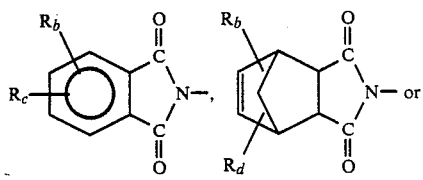

$R_b$ is hydrogen, halogen preferably fluorine, or lower ($C_1$-$C_3$) alkyl preferably methyl, $R_c$ is

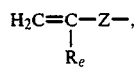

Z is —$(CH_2)_t$—, t is 0 to 4, $R_d$ is H or $R_c$, and $R_e$ is H or $CH_3$.

Preferably, $R_b$ is hydrogen, $R_d$ is hydrogen, n is 1 or 2, and t is 8 or 1.

Preferably, $R_a$ is

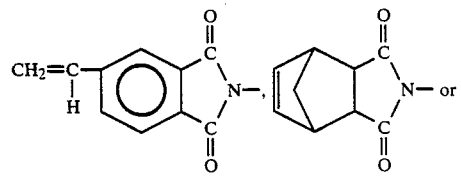

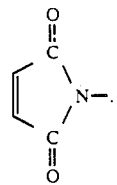

Generally speaking, this class of prepolymers may be prepared by reacting dicarboxylic acids, wherein the carboxyl groups are linked to adjacent carbon atoms, or derivatives thereof such as acid-esters or anhydrides, with the condensation product of the diamines of formula (5) and the tetracarboxylic acids or derivatives of formulae (3) or (4). The preferred end-capping compounds are vinyl-substituted ortho-phthalic acid anhydrides, nadic acid anhydrides and maleic acid anhydrides.

The diamine may be condensed first with the dianhydride and then the end-capping agent may be reacted with this intermediate condensation product. Alternatively, the diamine may be reacted with a mixture of the dianhydride and end-capping agent. The molar ratio of the diamine to dianhydride must be sufficient to provide terminal amino groups at the ends of the intermediate product for the purpose of reacting the product with the end-capping agent. Generally, the molar ratios of diamine to dianhydride will range from about 2:1 to about 4:3. The preferred diamines are the 6F-44, 6F-33, BDAF, ODA, mPDA and pPDA.

The preparation of bismaleimides prepolymers and the corresponding addition polyimides is generally shown in U.S. Pat. No. 4,173,700 to Green et al., which is incorporated herein by reference. The bismaleimides of the present invention may be characterized as having the structure:

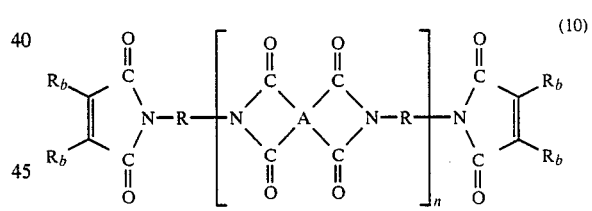
(10)

wherein n is 1 to 5, and R, A, and $R_b$ are the radicals as defined above. Preferably, $R_b$ is hydrogen or fluorine, and n is 1 or 2. The preferred end-capping agents are maleic anhydride and difluoromaleic anhydride.

The preparation of bisnadimide prepolymers and the corresponding addition polyimides is generally shown in U.S. Pat. No. 3,528,950 to Hyman, which is incorporated herein by reference. The bisnadimides of the present invention may be characterized as having the structure:

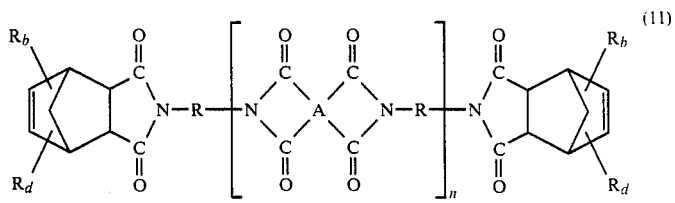
(11)

wherein n is 1 to 5, and R, A, $R_b$ and $R_d$ are radicals as defined above. Preferably, $R_b$ is hydrogen or methyl, $R_d$ is hydrogen, and n is 1 or 2. The preferred end-capping agent is 5-norbornene-2,3-dicarboxylic acid anhydride.

Another method of preparing addition polyimides and polyimide prepregs using nadic acid compounds is disclosed in U.S. Pat. No. 4,233,258 to St. Clair, U.S. Pat. No. 4,281,102 to St. Clair et al., and Johnston et al., "A Mechanistic Study of Polyimide Formation from Diester-Diacids," Journal of Polymer Science: Part A: Polymer Chemistry, Vol. 25, pp. 2175-2183 (1987), which are incorporated herein by reference. According to this approach a diamine, a nadic acid-ester, and a tetracarboxylic diacid-diester are dissolved in a lower alkyl alcohol such as a methanol or ethanol. The nadic acid-ester and tetracarboxylic diacid-diester may be made by refluxing stoichiometric amounts of the nadic anhydride and tetracarboxylic dianhydride with excess alcohol such as ethanol. The resulting solution is cooled to room temperature and the diamine is then added. The homogeneous mixture may then be used for prepregging onto fibers. The polymerization proceeds through two steps. The first step involves heating to cause imidization (120-230° C.) to occur resulting in limited chain extension to form low molecular weight norborene end-capped oligomers. In the second step, the norborene endcaps are crosslinked by heating to higher temperatures (275°-325° C.) Because this final reaction occurs without the release of volatile materials, high quality void-free composites may be fabricated. Typically, the solvents used in this type of system have been methanol and ethanol. However, it has been found that is is advantageous to use propylene glycol methyl ether (PGME) as a solvent in this system. By using PGME, certain environmental hazards associated with the handling and disposal of solvents such as methanol and ethanol are avoided. The monomer reactants may be dissolved in up to about a 50 weight percent solution using PGME as a solvent.

The following examples are illustrative of prepolymers and addition polyimides of this invention:

EXAMPLE 9

A four-necked flask fitted with a stirrer and maintained under a nitrogen atmosphere is charged with 4.88 g (0.011 moles) of 6F-44, 3.81 g (0.005moles) of 12F-DA , 90 ml of toluene and 10 ml of DMF. 1.08 g (0.011 moles) of maleic anhydride is added while stirring is continued. After 1 hour of stirring, 6.6 g of acetic anhydride and 0.5 g of sodium acetate is added and the mixture is stirred for an additional 1 hour. The mixture is then heated to 50° C. for 8 hours. The reaction product is then precipitated in an ice-water mixture, filtered, washed several times with water and dried overnight in a vacuum oven at 90° C., yielding a bismaleimide oligomeric material.

1.0 g of the bismaleimide oligomeric material is dissolved in 3.0 ml of NMP. The solution is spread on a glass plate to obtain a uniform film. The plate is dried in an air oven first at 90° C. for one hour and then at 270° C. for one hour to remove the solvent and cure the oligomeric material.

EXAMPLE 10

A 3-neck flask purged with nitrogen and fitted with a condenser, thermometer, and stirrer is charged with 4.88 gms (0.011 moles) of 6F-44 and 20 g of NMP under a nitrogen atmosphere. The mixture is stirred to obtain a clear solution. To the clear solution, 3.81 g (0.005 moles) of 12F-DA is added while stirring is continued. 1.86 g (0.011 moles) of cis-5-norbornene-endo-2,3-dicarboxylic acid anhydride (97% pure) (hereinafter "Nadic Anhydride") is then added also under continuous stirring. After charging with 24.45 g of NMP, the reaction mixture is stirred overnight at room temperature, resulting in a nadic-terminated polyamic acid.

To 65 g of the polyamic acid solution, 16.72 g of acetic anhydride and 1.67 g of 3-picoline is added. The reaction mixture is stirred at room temperature for about six hours. The resulting nadic-terminated oligomeric material is precipitated in methanol, isolated by filtration, washed with fresh methanol, and dried overnight in a vacuum oven at 85° C.

1.0 g of the nadic-terminated oligomeric material is dissolved in 3.0 ml of NMP. The solution is spread on a glass plate to obtain a uniform film. The plate is dried in an air oven first at 90° C. for one hour and then at 270° C. for one hour to remove the solvent and cure the oligomeric material.

Another class of addition-type polyimide prepolymers may be characterized as having the following structure:

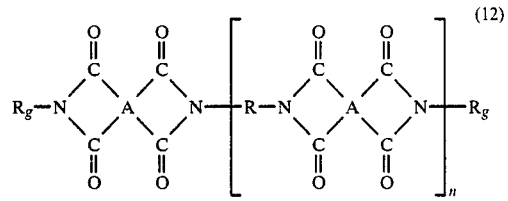

wherein n is 0 to 4, preferably n is 0 or 1, $R_g$ is

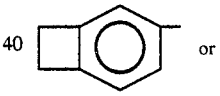 or

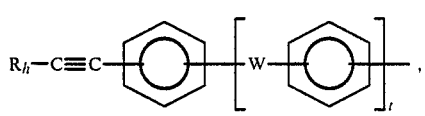

$R_h$ is H or

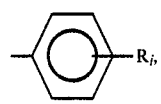

preferably H or —$C_6H_5$, $R_i$ is H, —O—$C_6H_5$ or —O—$C_6H_4$—$SO_2$—$C_6H_5$, preferably H, W is —O—, —S—, —$SO_2$—, —CO—, —$CH_2$—, —$C(CH_3)_2$— or —$C(CF_3)_2$—, and t is 0 to 4, preferably t is 0.

This class of prepolymers may be prepared by reacting end-capping amines with tetracarboxylic acids or derivatives of formulae (3) or (4) or with intermediate compounds having terminal anhydride, diacid, or acid-ester groups. The intermediates are obtained by reacting excess molar amounts of tetracarboxylic acids or derivatives of formulae (3) or (4) with diamines of formula (5). Generally, the molar ratios of dianhydride to diamine will range from 2:1 to 4:3. The intermediates are then reacted with end-capping amines. Alternatively, the dianhydride may be reacted with a mixture of the diamine and end-capping agent. The preferred diamines are 6F-44, 6F-33, BDAF, ODA, mPDA and pPDA.

The preferred end-capping amines are 4-aminobenzocyclobutene, aminoarylacetylenes, and phenylacetylenearylamines.

The preparation of bisbenzocyclobutene substituted imide oligomers and the corresponding addition polyimides is generally shown in Tan and Arnold, "Benzocyclobutene in Polymer Synthesis I. Homopolymerization of Bisbenzocyclobutene Aromatic Imides to Form High-Temperature Resistant Thermosetting Resins," Journal of Polymer Science, Polymer Chemistry Edition, Vol 26, pp. 18-19, (1988), which is incorporated herein by reference. The benzocyclobutene substituted imide oligomers of the present invention may be characterized as having the structure:

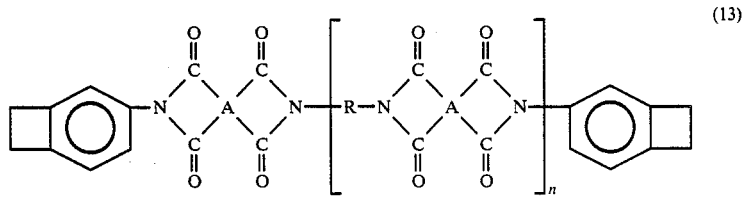

(13)

wherein n is 0 to 4, and R and A are as defined above. Preferably, n is 0 or 1.

The preparation of acetylene terminated imide oligomers and the corresponding addition polyimides is generally shown in U.S. Pat. No. 4,276,407 to Bilow et al. and PCT Publication No. WO 81/01293, Bilow et al., entitled "Acetylene Terminated Imide Oligomers Having Improved Solubilities and Lower Melting Points," which are incorporated herein by reference. The acetylene and phenylacetylene terminated imide oligomers of the present invention may be characterized as having the structure:

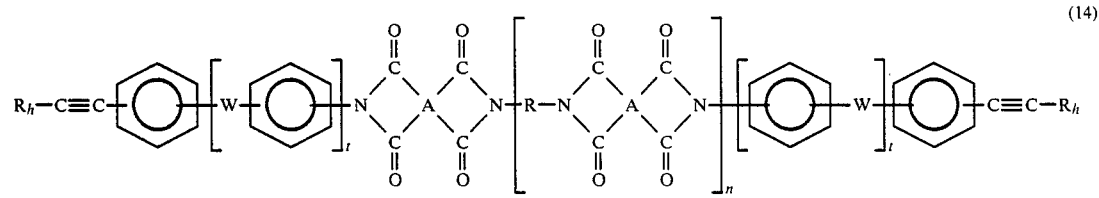

(14)

wherein n is 0 to 4, t is 0 to 4, and R, A, $R_h$, and W are defined as above. Preferably, n is 0 or 1, and t is 0.

Suitable end capping amines having terminal acetylene or phenylacetylenyl groups are those having the structure:

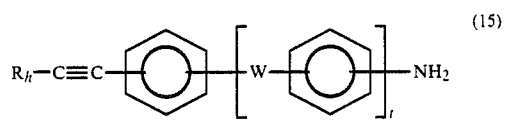

(15)

wherein t is 0 to 4, preferably t is 0, and $R_h$ and W are as defined above. The preferred acetyleneamine is 3-aminophenylacetylene and the preferred phenylacetylenylamine is 1-amino-3-phenylacetylenylbenzene.

The preparation of benzocyclobutene-alkyne imide monomers and the corresponding addition polyimides is generally shown in U.S. Pat. No. 4,675,370 to Tan et al., which is incorporated herein by reference. The benzocyclobutene-alkyne monomers and oligomers of the present invention may be characterized as having the structure:

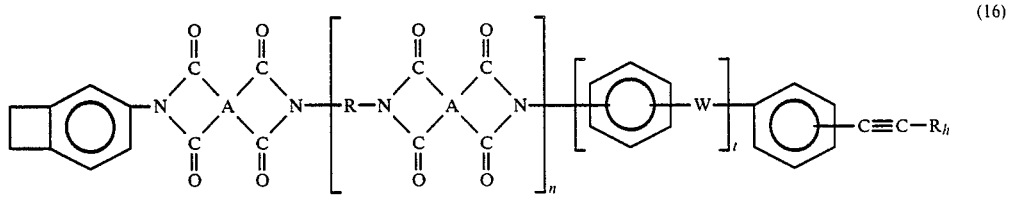

(16)

wherein n is 0 to 4, t is 9 to 4, $R_h$ is hydrogen or phenyl, preferably $R_h$ is phenyl, and R, A and W are as defined above. Preferably, n is 0, and t is 0.

The following examples are illustrative of imide oligomers and addition polyimides of this invention:

EXAMPLE 11

A solution 8.38 g (0.011 moles) of 12F-DA in 75 ml of NMP at 50° C. is charged into a three-necked flask equipped with stirrer under a nitrogen atmosphere. After stirring for 30 minutes, a solution of 0.0225 moles of 4-aminobenzocyclobutene in 10 ml of NMP is added all at once. 75 ml of toluene is then added and the reaction mixture is refluxed (at about 143° C.) for 12 hours employing a Dean-Stark trap to remove the water. The solvent is distilled off using a mild vacuum. A residue remains which is precipitated using ethanol. A benzocyclobutene-terminated monomer product is obtained which is washed several times with ethanol and dried overnight in a vacuum oven at 90° C.

1.0 g of the benzocyclobutene-terminated monomer is dissolved in 3.0 ml of NMP. The solution is spread on a glass plate to obtain a uniform film. The plate is dried in an air oven first at 90° C. for one hour and then at 270° C. for one hour to remove the solvent and cure the monomer.

EXAMPLE 12

A solution of 3.34 g (0.01 moles) of 6F-44 in 50 ml of NMP is added dropwise to a solution of 16 g (0.021 moles) of 12F-DA in 75 ml of NMP at 50° C. in a three-necked flask equipped with stirrer under a nitrogen atmosphere. After heating the reaction contents at 50° C. for 30 minutes, a solution of 3.6325 g (0.0225 moles) of 3-aminophenylacetylene in 10 ml of NMP is added all at once. 75 ml of toluene is then added and the reaction mixture is refluxed (at about 143° C.) for 12 hours employing a Dean-Stark trap to remove the water. The solvent is distilled off using a mild vacuum. A brown oily residue remains which is precipitated using ethanol. A brown colored product is obtained which is washed several times with ethanol and dried overnight in a vacuum oven at 90° C.

1.0 g of the acetylene-terminated oligomeric material is dissolved in 3.0 ml of NMP. The solution is spread on a glass plate to obtain a uniform film. The plate is dried in an air oven first at 90° C. for one hour and then at 270° C. for one hour to remove the solvent and cure the monomer.

The invention provides copolymers prepared by reacting the acetylene or phenylacetylene terminated oligomers of formula (14) with other known acetylene or phenylacetylene terminated monomers and oligomers. Various acetylene terminated oligomers are described in, for example, U.S. Pat. Nos. 4,100,138 and 4,276,407 to Bilow et al., which are incorporated herein by reference. U.S. Pat. No. 4,100,138 also describes the copolymerization of acetylene terminated polyimide oligomers with diethynylbenzene. Arylether compounds having terminal phenylethynyl groups are described in U.S. Pat. No. 4,513,131 to Reinhardt et al., which is incorporated herein by reference.

The invention further provides compositions of component (A) comprising known polymides or copolyimides such as those described in U.S. Pat. Nos. 3,342,774 to Hoegger; 3,356,648 to Rogers; 3,424,718 to Angelo; 3,649,601 to Critchley et al.; 3,926,913 to Jones et al.; 3,959,350 to Rogers; 4,111,906 to Jones et al.; 4,477,648 to Jones et al.; 4,535,101 to Lee et al.; 4,595,548 to St. Clair et al.; 4,603,061 to St. Clair et al.; and 4,612,361 to Peters; which are herein incorporated by reference; or a polyimide of formula (1); or mixtures thereof; and component (B) comprising an addition-type polyimide monomer, oligomer or prepolymer of formulae (9), (10), (11), (12), (13), (14) or (16). In another aspect, the invention provides compositions wherein component (A) is a polyimide of formula (1) and wherein component (B) is a known addition-type polyimide monomer, oligomer or prepolymer such as those described in U.S. Pat. Nos. 4,173,700 to Green et al.; 3,528,950 to Hyman, 4,233,258 to St. Clair, 4,281,102 to St. Clair et al.; 4,276,407 to Bilow et al.; 4,675,370 to Tan et al.; the Tan and Arnold publication referred to above; and PCT Publication No. WO 81/01293, Bilow et al.; all of which are incorporated herein by reference. The compositions are useful for producing films, composites and as matrix resins. When the compositions are cured, the component (B) material is polymerized forming interpenetrating networks or semi-interpenetrating networks which physically bond the molecules of the component (A) polymer in the network.

Preferably, component (A) is present in the composition in the range of from about 90 to about 10, more preferably from about 80 to about 20, percent by weight of the total combined weight of components (A) and (B). Preferably, component (B) is present in the composition in the range of from about 10 to about 90, more preferably from about 20 to about 80, percent by weight of the total combined weight of components (A) and (B).

The following examples are illustrative of the invention:

EXAMPLE 13

A composition is prepared by dissolving 1.0 g of SIXEF-44 TM polyimide (a polyimide prepared from 6F-DA dianhydride and 6F-44 diamine), available from Hoechst Celanese Corporation, Somerville, N.J., and 1.0 g of bismaleimide oligomeric material prepared according to Example 9 in 10.0 ml of NMP. The solution is spread over a glass plate to obtain a uniform film. The coated plate is dried in an air oven first at 90° C. for one hour and then at 270° C. for one hour to evaporate the residual solvent and to cause cross-linking of the bismaleimide oligomeric material.

EXAMPLE 14

A composition is prepared by dissolving 1.0 g of SIXEF-44 TM polyimide (a polyimide prepared from 6F-DA dianhydride and 6F-44 diamine), available from Hoechst Celanese Corporation, Somerville, N.J., and 1.0 g of nadic-terminated oligomeric material prepared according to Example 10 in 10.0 ml of NMP. The solution is spread over a glass plate to obtain a uniform film. The coated plate is dried in an air oven first at 90° C. for one hour and then at 270° C. for one hour to evaporate the residual solvent and to cause cross-linking of the bisnadimide oligmeric material.

EXAMPLE 15

A composition is prepared by dissolving 1.0 g of SIXEF-44 TM polyimide (a polyimide prepared from 6F-DA dianhydride and 6F-44 diamine), available from Hoechst Celanese Corporation, Somerville, N.J., and 1.0 g of acetylene-terminated oligomer prepared according to Example 12 in 10.0 ml of NMP. The solution is spread over a glass plate to obtain a uniform film. The coated plate is dried in an air oven first at 90° C. for one hour and then at 270° C. for one hour to evaporate the residual solvent and to cause cross-linking of the acetylene-terminated oligomer.

The invention further provides bis(amino-imide) compounds useful as curing agents for polyfunctional epoxy resins. The bis(amino-imide) compounds of the present invention may be characterized as having the structure:

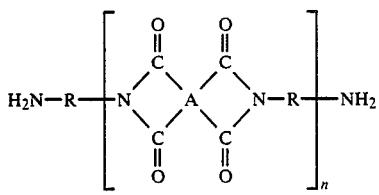

(17)

wherein n is 1 to 5, and R and A are radicals as defined above. Preferably n is 1 or 2.

The bis(amino-imide) compounds may be prepared by known methods such as those described in U.S. Pat. No. 4,244,857 to Serafini et al., which is incorporated herein by reference. They are conveniently prepared by reacting of formulae (3) or (4) with diamines of formula (5). The molar ratio of diamine to dianhydride is preferably in the range of about 2:1 to about 4:3.

The following example is illustrative of the preparation of the bis(amino-imide) compounds of the present invention:

EXAMPLE 16

A 3-neck flask purged with nitrogen and fitted with a condenser, thermometer, and stirrer is charged with 6.68 g (0.02 moles) of 6F-44 and 20 g of NMP under a nitrogen atmosphere. The mixture is stirred to obtain a clear solution. 7.62 g (0.01 moles) of 12F-DA is added while stirring is continued. After the addition is completed, the solution is stirred at room temperature under nitrogen for two hours. The solution is then refluxed for two hours. After cooling, the solution is poured into 400 ml of distilled water with vigorous stirring. The precipitate is filtered, washed with water, and dried overnight in a vacuum oven at 85° C. to yield the bisaminoimide.

The invention also provides epoxy resin compositions. The epoxy resin composition comprises a polyfunctional epoxy resin and a curing agent. The curing agent may be a bis(amino-imide) compound of formula (17).

The polyfunctional epoxy resins to which the invention relates are widely known and described in the literature and need not be redescribed herein.

The ratio by weight of epoxy resin to curing agent is preferably in the range of from about 10:90 to about 90:10, more preferably of from about 20:80 to about 80:20.

The compositions of epoxy resins and curing agent are used to impregnate fibers, such as carbon, boron and glass, and may also be filled with particulate fillers to provide high performance fiber reinforced plastic articles or filled epoxy resins which are used to fabricate a wide variety of molded articles. The preparation of epoxy resin compositions and molded articles therefrom is described in the above-referenced U.S. Pat. No. 4,244,857 to Serafini et al. and in D. A. Scola, "Synthesis and Characterization of Bisimide Amines and Bisimide Amine-Cured Epoxy Resins," Polymer Composites, Vol. 4, No. 3, pp. 154–161, (July, 1983), which is incorporated herein by reference. The compositions may also be used as adhesives.

The following example is illustrative of the invention:

EXAMPLE 17

A solution of 16 g of the bis(amino-imide) compound prepared in Example 16 in 10 g of BLO solvent is mixed with 10 g of a bisphenol A diepoxide (Interez 510) at room temperature. The mixture is cast on a glass plate and heated at 110° C. for 3 hours resulting in a cured film.

The solvent soluble polyimides and their polyamic acid precursors of the invention may be used in the preparation of photosensitive compositions and processed by conventional techniques to provide thermally stable relief patterns. These photosensitive compositions are useful in many applications such as photopolymerizable varnishes or protective layers such as passivation overcoat films, planarization layers in microelectronic circuits, insulating layers for multi-layered hybrid circuits and as photoresists that provide relief structures of good definition on substrates such as silicon chips, polymeric films and metal plates. They provide polymeric layers or relief structures that possess high thermal and radiation stability, excellent mechanical properties and high insulating properties. In other applications such as printing plates, the tough mechanical properties of the photopolymerizable compositions of the invention provide a means to make printing plates having the capability of giving long printing runs.

In one form, the photosensitive compositions of the invention comprise a mixture of a solvent soluble polyimide of the invention, a photoinitiator and a photopolymerizable compound containing at least two terminal ethylenically unsaturated groups.

Suitable photopolymerizable material comprises an addition polymerizable, non-gaseous (boiling temperature above 100° C. at normal atmospheric pressure), ethylenically-unsatrurated compound containing at least two terminal ethylenic groups, and being capable of forming a high molecular weight polymer by free radical initiated, chain propagating addition polymerization. Illustrative examples include tetraethylene glycol dimethacrylate, ethylene glycol dimethacrylate, trimethylol propane trimethacrylate, trimethylol propane triacrylate, polyethylene glycol (200) or (600) diacrylate, diethylene glycol dimethacrylate, pentaerythritol tetraacrylate, pentaerythritol triacrylate, 1,6-hexanediol dimethacrylate, dipentaerythritol monohydroxypentaacrylate, ethoxylated bisphenol A dimethacrylate, tripropylene glycol diacrylate, tris(2-hydroxyethyl)isocyanurate, trimethylacrylate tris(2-hydroxyethyl)triacrylate, glycerol diacrylate, glycerol triacrylate, hexamethylene diamine, diacrylamide and mixtures thereof.

Suitable photoinitiators useful in the practice of the invention are disclosed in U.S. Pat. Nos. 4,464,457; 4,465,758 and 4,619,998 which are incorporated herein by reference. A large number of substances can be used in the mixture of the present invention as polymerization intitiators which can be activated by radiation, particularly actinic light. Examples are benzoin and its derivatives, trichloromethyl-s-triazines, 1,3-bistrichloromethyl-5-(para-biphenyl)triazine-2,4,6; 1,3-bistrichloromethyl-5-(para-stilbenyl)triazine-2,4,6; acridine derivatives, for example, 9-phenylacridine, 9-p-methoxyphenylacridine, 9-acetylaminoacridine and benz(l)-acridine. Other examples are phenazine derivatives, for example, 9,10-dimethylbenz(a)phenazine and 10-methoxybenz(a)phenazine, quinoxaline derivatives, for example, 6,4',4''-trimethoxy-2,3-diphenylquinoxaline and 4',4''-dimethoxy2,3-diphenyl-5-azaquinoxaline. The initiators are generally employed in the present invention in an amount of 0.01 to 20, preferably 0.05 to 10 percent by weight, relative to the non-volatile components of the mixture.

The mixture according to the present invention generally contains 20 to 90, preferably 30 to 80, percent by weight of solvent soluble polyimide and 80 to 10, preferably 70 to 20, percent by weight of polymerizable compounds, relative in each case to the total amount of non-volatile ethylenically unsaturated monomer and polyimide components.

The mixture can contain, as further conventional components, polymerization inhibitors, oxygen scavengers, hydrogen donors, sensitometric regulators, dyes, pigments, plasticizers and thermally activatable crosslinking agents.

It is generally advantageous to substantially isolate the compositions of the present invention from the influence of atmospheric oxygen during photopolymerization. If the composition is used in the form of a thin copying layer, it is recommended that a suitable cover film with a low permeability to oxygen be applied to the layer.

Leuco bases of triarylmethane dyes that are suitable for use in the present invention include those of Crystal Violet, Victoria Blue BH, Victoria Pure Blue BOH, Methyl Violet, and Acilan Violet S.

Suitable actinic radiation to which the composition according to the present invention is sensitive is any electromagnetic radiation whose energy is sufficient to initiate polymerization. Visible and ultraviolet light, x-rays and electron radiation are particularly suitable Laser radiation in the visible and UV range can also be used. Short-wavelength visible and near-UV light is preferred.

The photosensitve compositions of the invention may be employed in solution which can be applied to a substrate by any conventinal method, such as roller coating, dipping, spraying, whirling and spin coating. They may be prepared into and used as dry films as is taught in U.S. Pat. No. 3,469,982 to Celeste which is incorporated herein by reference.

Suitable substrates include silicon, aluminum, glass, polymeric resin boards and films, silicon dioxide, doped silicon dioxide nitride, tantalum, copper, polysilicone ceramics and aluminum/copper mixtures Suitable application solvents include N-methyl- pyrrolidone, dimethylformamide, γ-butyrolactone, acetone, diglyme, tetrahydrofuran, propylene glycol methyl ether, propylene glycol methyl ether acetate, and mixtures thereof The photosensitive composition after exposure may be developed by any suitable organic solvent, e.g., γ-butyrolactone, toluene, propylene glycol methyl ether/toluene, N-methylpyrrolidone/toluene, acetone/water mixtures etc.

The following examples are illustrative of the photosensitive compositions of the invention:

EXAMPLE 18

A photosensitive composition is prepared using the solvent soluble polyimide of Example 2:

| | |
|---|---|
| Example 2 Polyimide | 4.0 grams |
| Pentaerythritol triacrylate | 1.5 grams |
| 1,3-bistrichloromethyl-5-(p-stilbenyl)triazine-2,4,6 | 0.1 grams |
| Dye | 0.03 grams |
| Diglyme/BLO (50/50) | 16.0 grams |

The resulting photosensitive compostion is filtered under pressure and is roller coated on an anodized aluminum plate. The coated plate is pre-baked at 90° C. for 3 minutes to obtain a resist film. The film is then overcoated with a polyvinyl alcohol protective layer (10% in water) and prebaked at 90° C. for 2 minutes. The film is then covered with a photomask having a striped pattern so that the film and the photomask are in tight contact. The film is exposed through an Addalux vacuum printer (2KW, photopolymer lamp/UV broad band radiation) for an irradiation time range of 300 sec. After the irradiation, the coating is first rinsed with hot water to remove the polyvinyl alcohol overcoat, then is developed with a mixed solution of 4 volume of BLO and 1 volume of toluene and rinsed with n-hexane to give a negative image.

Other developers include a mixture of toluene/NMP (9:1) and acetone/water (7:3).

EXAMPLE 19

A photosensitive composition is prepared and processed in accordance with the procedure of Example 18 using the solvent soluble polyimide of Example 3:

| | |
|---|---|
| Example 3 Polyimide | 2.0 grams |
| Pentaerythritol triacrylate | 0.4 grams |
| 1,3-bistrichloromethyl-5-(p-stilbenyl)triazine-2,4,6 | 0.3 grams |
| Diglyme/BLO (50/50) | 15.0 grams |

Similarly, the polyamic acid precursors of the polyimides of the invention may be substituted for the fully imidized polymers of the forgoing examples 18 and 19. However, after the image is developed, the film is converted to a polyimide by baking at 275°–350° C. for 0.5 to 3 hours.

The forgoing examples illustrate the use of the polymers of the invention as negative acting resists. However, they may also be used to produce positive acting compositions as illustrated by the teachings of U.S. Pat. No. 4,093,461 which are incorporated herein by reference. In these compositions, the polyamic acid precursor is mixed with a photosensitive orthoquinone or naphthoquinone diazide and processed in the conventional manner to produce a positive relief structure.

What is claimed is:

1. A polyimide polymer having groups of the structure:

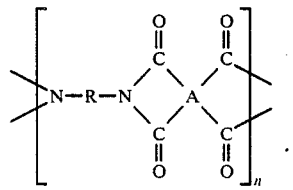

wherein n is the number of repeating groups,
A is

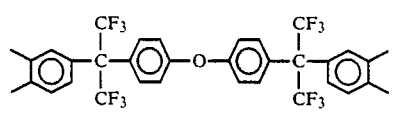

and R is a divalent organic radical.

2. The polyamide of claim 1, wherein R is selected from the group consisting of

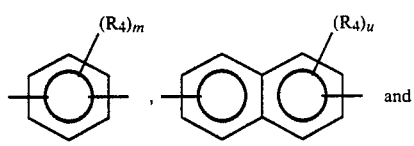

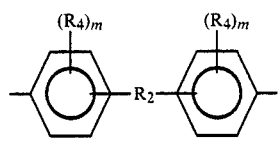

wherein $R_2$ is a carbon-carbon bond, —O—, —S—, —SO$_2$—, —CO—, —(CH$_2$)$_r$—,

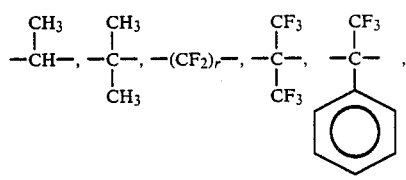

—O—(CH$_2$—CH$_2$—O)$_r$—, —O—(CF$_2$)$_s$—O—,

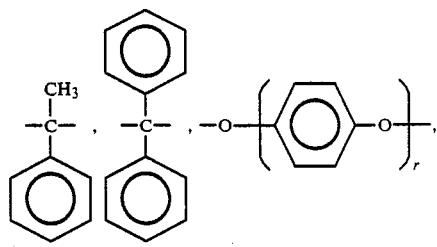

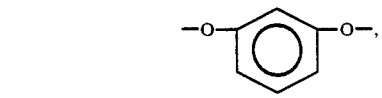

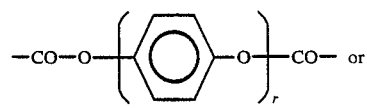

wherein $R_3$ is a carbon-carbon bond, —S—, —SO$_2$—, —CO—, —CH$_2$—, —C$_2$H$_4$—,

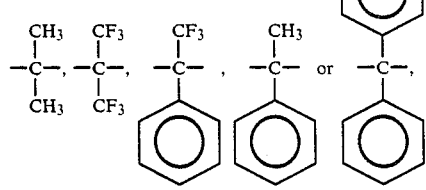

$R_4$ is halogen, hydroxy, lower (C$_1$-C$_6$) alkyl or lower (C$_1$-C$_6$) alkoxy, m is 0 to 2, r is 1 to 4, and s is 1 to 5.

3. Polyamide-acid polymeric material having groups of the structure:

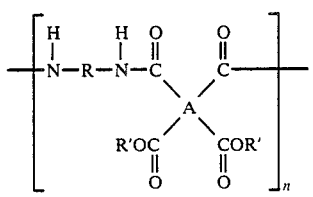

wherein n is the number of repeating groups,

A is

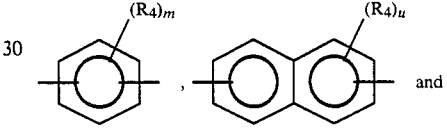

R is a divalent organic radical, and
R' is hydrogen or a monovalent organic radical.

4. The polyamide-acid polymeric material of claim 3, wherein R is selected from the group consisting of

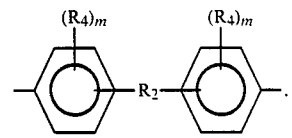

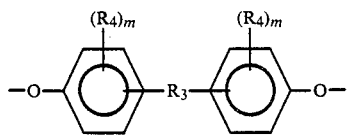

wherein $R_2$ is a carbon-carbon bond, —O—, —S—, —SO$_2$—, —CO—, —(CH$_2$)$_r$—,

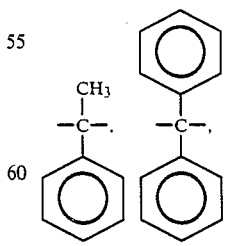

—O—(CH$_2$—CH$_2$—O)$_r$—, —O—(CF$_2$)$_s$—O—,

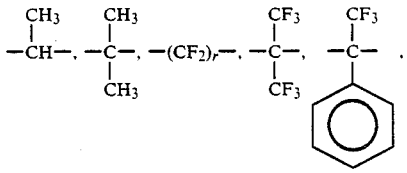

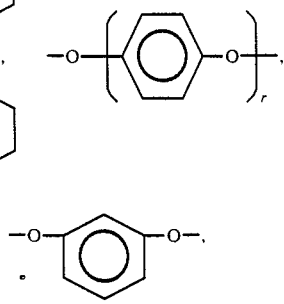

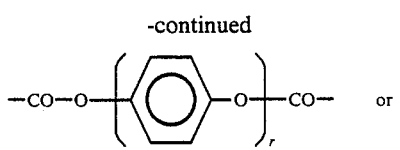 or

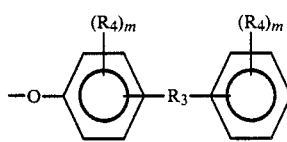

wherein $R_3$ is a carbon-carbon bond, —S—, —SO$_2$—, —CO—, —CH$_2$—, —C$_2$H$_4$—,

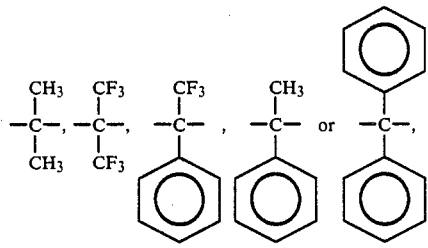

$R_4$ is halogen, hydroxy, lower (C$_1$-C$_6$) alkyl or lower (C$_1$-C$_6$) alkoxy, m is 0 to 2, r is 1 to 4, and s is 1 to 5.

5. Polyamide-acid polymeric material prepared by reacting a dianhydride having the formula:

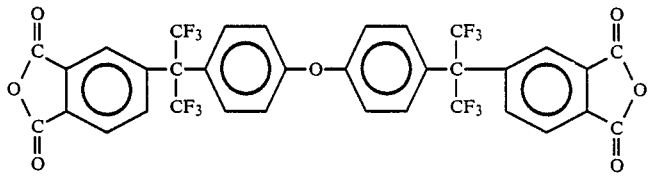

and at least one diamine having the formula:

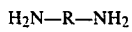

wherein R is a divalent organic radical.

6. The polyamide-acid polymeric material of claim 5, wherein the diamine is selected from the group consisting of:
m-phenylene diamine;
p-phenylene diamine;
1,3-bis(4-aminophenyl) propane;
2,2-bis(4-aminophenyl) propane;
4,4'-diamino-diphenyl methane;
1,2-bis(4-aminophenyl) ethane;
1,1-bis(4-aminophenyl) ethane;
2,2'-diamino-diethyl sulfide;
bis(4-aminophenyl) sulfide;
2,4'-diamino-diphenyl sulfide;
bis(3-aminophenyl) sulfone;
bis(4-aminophenyl) sulfone;
4,4'-diamino-dibenzyl sulfoxide;
bis(4-aminophenyl) ether;
bis(3-aminophenyl) ether;
bis(4-aminophenyl) diethyl silane;
bis(4-aminophenyl) diphenyl silane;
bis(4-aminophenyl) ethyl phosphine oxide;
bis(4-aminophenyl) phenyl phosphine oxide;
bis(4-aminophenyl)-N-phenylamine;
bis(4-aminophenyl)-N-methylamine;
1,2-diamino-naphthalene;
1,4-diamino-naphthalene;
1,5-diamino-naphthalene;
1,6-diamino-naphthalene;
1,7-diamino-naphthalene;
1,8-diamino-naphthalene;
2,3-diamino-naphthalene;
2,6-diamino-naphthalene;
1,4-diamino-2-methyl-naphthalene;
1,5-diamino-2-methyl-naphthalene;
1,3-diamino-2-phenyl-naphthalene;
4,4'-diamino-biphenyl;
3,3'-diamino-biphenyl;
3,3'-dichloro-4,4'-diamino-biphenyl;
3,3'-dimethyl-4,4'-diamino-biphenyl;
3,4'-dimethyl-4,3'-diamino-biphenyl;
3,3'-dimethoxy-4,4'-diamino-biphenyl;
4,4'-bis(4-aminophenoxy)-biphenyl;
2,4-diamino-toluene;
5-diamino-toluene;
3,3'-butoxy-4,4'-diamino-biphenyl;
2,6-diamino-toluene;
3,5-diamino-toluene;
1,3-diamino-2,5-dichloro-benzene;
1,4-diamino-2,5-dichloro-benzene;
1-methoxy-2,4-diamino-benzene;
1,4-diamino-2-methoxy-5-methyl-benzene;
1,4-diamino-2,3,5,6-tetramethyl-benzene;
1,4-bis(2-methyl-4-amino-pentyl)-benzene;
1,4-bis(1,1-dimethyl-5-amino-pentyl)-benzene;
1,4-bis(4-aminophenoxy)-benzene;
o-xylylene diamine;
m-xylylene diamine;
p-xylylene diamine;
3,3'-diamino-benzophenone;
4,4'-diamino-benzophenone;
2,6-diamino-pyridine;
3,5-diamino-pyridine;
1,3-diamino-adamantane;
3,3'-diamino-1,1'-diadamantane;
bis(4-amino-cyclohexyl) methane;
1,5-diamino-pentane;
1,6-diamino-hexane;
1,7-diamino-heptane;
1,8-diamino-octane;
1,9-diamino-nonane;
1,10-diamino-decane;
1,7-diamino-3-methyl-heptane;
1,7-diamino-4,4-dimethyl-heptane;
2,11-diamino-dodecane;
1,3-bis(3-aminopropoxy) ethane;
1,3-diamino-2,2-dimethyl-propane;
1,6-diamino-3-methoxy-hexane;
1,6-diamino-2,5-dimethyl-hexane;
1,7-diamino-2,5-dimethyl-heptane;
1,9-diamino-5-methyl-nonane;
1,4-diamino-cyclohexane;
2,5-diamino-1,3,4-oxadiazole;

N-(3-aminophenyl)-4-aminobenzamide;
4-aminophenyl-3-aminobenzoate;
2,2-bis(4-aminophenyl) hexafluoropropane;
2,2-bis(3-aminophenyl) hexafluoropropane;
2,2-bis[4-(4-aminophenoxy)phenyl] hexafluoropropane;
2,2-bis[4-(2-chloro-4-aminophenoxy)phenyl] hexafluoropropane;
1,1-bis(4-aminophenyl)-1-phenyl-2,2,2-trifluoroethane;
1,1-bis[4-(4-aminophenoxy)phenyl]-1-phenyl-2,2,2-trifluoroethane;
1,4-bis(3-aminophenyl)buta-1-ene-3-yne;
1,3-bis(3-aminophenyl)hexafluoropropane; and
1,5-bis(3-aminophenyl)decafluoropentane.

7. Copolyamide-acid polymeric material prepared by reacting a dianhydride having the formula:

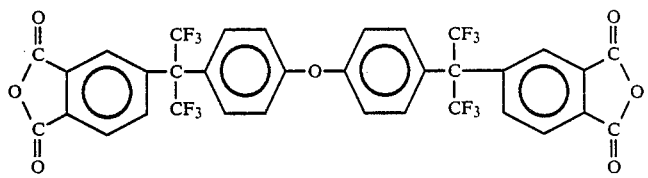

at least one diamine having the formula:

$H_2N-R-NH_2$ wherein R is a divalent organic radical; and at least one dianhydride having the formula:

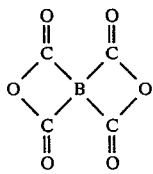

wherein B is a tetravalent organic radical having at least 4 carbon atoms.

8. An addition-type polyimide prepolymer having the structure:

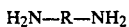

wherein n is 1 to 5,
R is a divalent organic radical,
A is

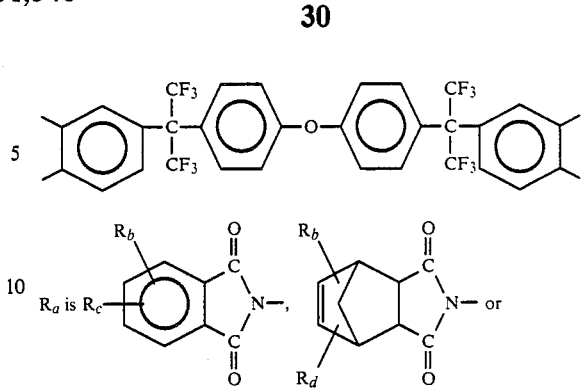

$R_a$ is $R_c$, $R_b$ is hydrogen, halogen or lower ($C_1$-$C_3$) alkyl,
$R_c$ is $H_2C=C-Z-$,
       $|$
       $R_e$ Z is $-(CH_2)_t-$,
$R_d$ is H or $R_c$,
$R_e$ is H or $CH_3$, and t is 0 to 4.

9. A bisnadimide prepolymer having the structure:

wherein n is 1 to 5,
R is a tetravalent organic radical, and
A is

10. A bismaleimide prepolymer having the structure:

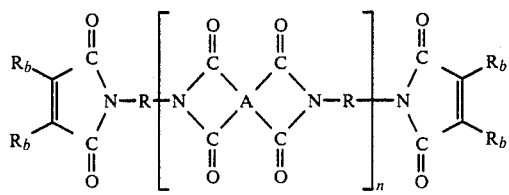

wherein n is 1 to 5,
R is a divalent organic radical,

A is

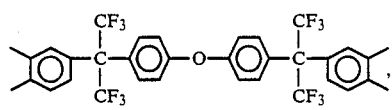

and $R_b$ is hydrogen, halogen or lower ($C_1$-$C_3$) alkyl.

11. An addition-type polyimide prepolymer having the structure:

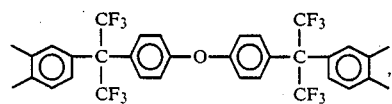

wherein n is 0 to 4,
R is a divalent organic radical,
A is

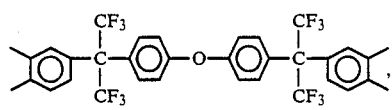

$R_g$ is

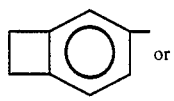 or

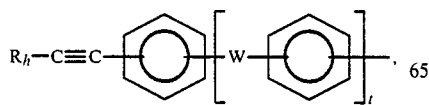

$R_h$ is H or

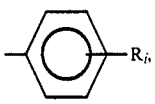

$R_i$ is H, —O—$C_6H_5$ or —O—$C_6H_4$—$SO_2$—$C_6H_5$,
W is —O—, —S—, —$SO_2$—, —CO—, —$CH_2$—, —C($CH_3$)$_2$— or —(CF$_3$)$_2$—, and t is 0 to 4.

12. An acetylene substituted imide oligomer having the structure:

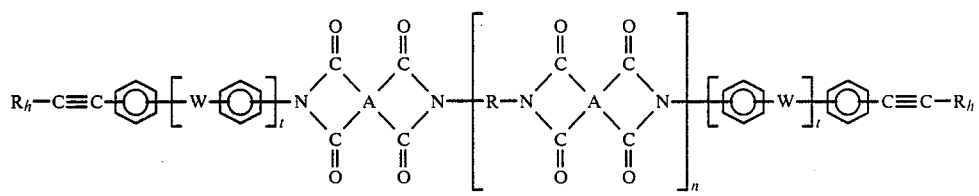

wherein n is 0 to 4,
t is 0 to 4,
R is a divalent organic radical,
A is

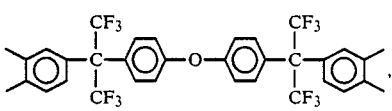

$R_h$ is H or

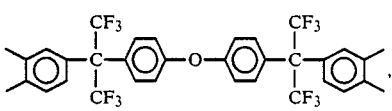

$R_i$ is H, —O—$C_6H_5$ or —O—$C_6H_4$—$SO_2$—$C_6H_5$, and
W is —O—, —S—, —$SO_2$—, —CO—, —$CH_2$—, —C($CH_3$)$_2$— or —C(CF$_3$)$_2$—.

13. A benzocyclobutene substituted imide oligomer having the structure:

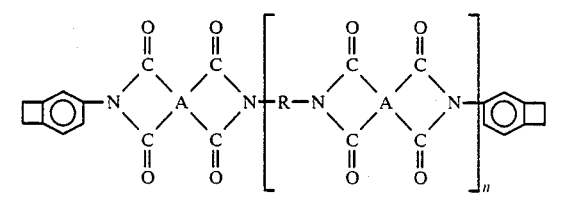

wherein n is 0 to 4,
R is a divalent organic radical, and
A is

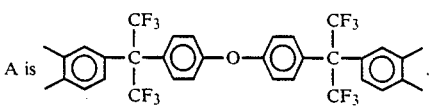

14. An imide oligomer having the structure:

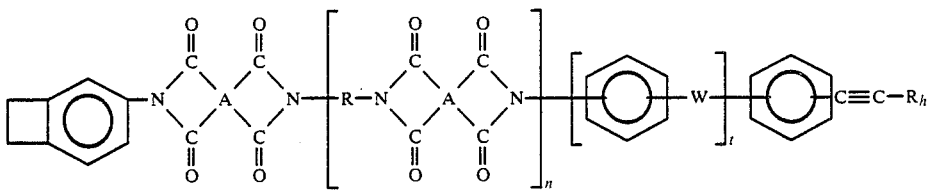

wherein n is 0 to 4,
R is a divalent organic radical, and
A is

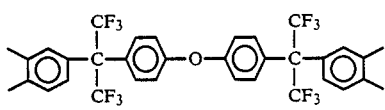

$R_h$ is H or

$R_i$ is H, —O—$C_6H_5$ or —O—$C_6H_4$—$SO_2$—$C_6H_5$,
W is —O—, —S—, —$SO_2$—, —CO—, —$CH_2$—, —C($CH_3$)$_2$— or —($CF_3$)$_2$—, and t is 0 to 4.

15. A photosensitive composition comprising a polyimide according to claim 1, a photopolymerizable compound containing at least two terminal ethylenically unsaturated groups and a photoinitiator.

16. A photosensitive composition comprising a polyamide-acid polymeric material according to claim 3, a photopolymerizable compound containing at least two terminal ethylenically unsaturated groups and a photoinitiator.

17. A photosensitive composition comprising a polyamide-acid polymeric material according to claim 3 and a light sensitive orthoquinone diazide or ortho naphthoquinone diazide.

18. A copolyimide polymer prepared from a copolyamide polymeric material of claim 7.

19. A polyimide polymer prepared from a polyimide prepolymer of claim 8.

20. A polyimide polymer prepared from a bisnadimide prepolymer of claim 9.

21. A polyimide polymer prepared from a bismaleimide prepolymer of claim 10.

22. A polyimide polymer prepared from a polyimide prepolymer of claim 11.

23. A polyimide polymer prepared from an imide oligomer of claim 12.

24. A polyimide polymer prepared from an imide oligomer of claim 13.

25. A polyimide polymer prepared from an imide oligomer of claim 14.

26. An article fabricated from a polyimide polymer of claim 1.

27. An article fabricated from a polyamide-acid polymeric material of claim 3.

28. An article fabricated from a polyamide-acid polyameric material of claim 5.

29. An article fabricated from a copolyamide-acid polymeric material of claim 7.

30. An article fabricated from a copolyimide of claim 18.

31. An article fabricated from a polyimide prepolymer of claim 8.

32. An article fabricated from a polyimide prepolymer of claim 9.

33. An article fabricated from a bismaleimide prepolymer of claim 10.

34. An article fabricated from a polyimide prepolymer of claim 11.

35. An article fabricated from an imide oligomer of claim 12.

36. An article fabricated from an imide oligomer of claim 13.

37. An article fabricated from an imide oligomer of claim 14.

38. A polymer composition comprising a solvent soluble thermoplastic polyimide polymer and a thermoset polyimide polymer prepared from an addition-type polyimide prepolymer of claim 8.

39. A polymer composition comprising a solvent soluble thermoplastic polyimide polymer and a thermoset polyimide polymer prepared from an addition-type polyimide prepolymer of claim 11.

40. A polymer composition comprising a polyimide polymer of claim 1 and a thermoset polyimide polymer prepared from an addition-type polyimide monomer, oligomer or prepolymer having a reactive endcap group of the structure:

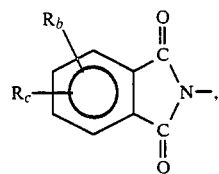

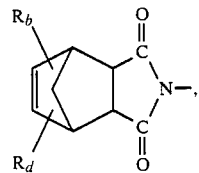

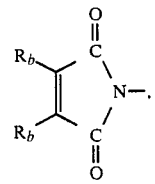

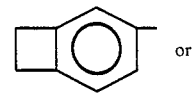

-continued
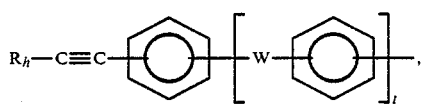
wherein $R_b$ is hydrogen, halogen or lower ($C_1$-$C_3$)alkyl, $R_c$ is
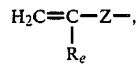
$R_d$ is H or $R_c$,
$R_e$ is H or $CH_3$,
$R_h$ is H or
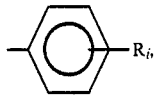
$R_i$ is H, $-O-C_6H_5$ or $-O-C_6H_4-SO_2-C_6H_5$,
Y is $-O-$, $-S-$, $-SO_2-$, $-CO-$, $-Ch_2-$, $-C(CH_3)_2-$ or $-(CF_3)_2-$,
Z is $-(CH_2)_t-$, and t is 0 to 4.
* * * * *